(12) United States Patent
Yan

(10) Patent No.: US 9,737,299 B2
(45) Date of Patent: Aug. 22, 2017

(54) END EFFECTOR, CARTRIDGE ASSEMBLY THEREOF, AND SURGICAL INSTRUMENT

(71) Applicant: REACH SURGICAL INC., Tianjin (CN)

(72) Inventor: Zheng Yan, Tianjin (CN)

(73) Assignee: REACH SURGICAL INC., Tianjin (CN)

( * ) Notice: Subject to any disclaimer, the term of this patent is extended or adjusted under 35 U.S.C. 154(b) by 0 days.

(21) Appl. No.: 15/457,033

(22) Filed: Mar. 13, 2017

(65) Prior Publication Data

US 2017/0189023 A1 Jul. 6, 2017

Related U.S. Application Data

(63) Continuation-in-part of application No. PCT/CN2015/088102, filed on Aug. 26, 2015.

(30) Foreign Application Priority Data

Sep. 12, 2014 (CN) .......................... 2014 1 0461885
Sep. 12, 2014 (CN) ...................... 2014 2 0522487 U

(51) Int. Cl.
 *A61B 17/072* (2006.01)
(52) U.S. Cl.
 CPC ...... *A61B 17/072* (2013.01); *A61B 17/07207* (2013.01); *A61B 2017/07257* (2013.01); *A61B 2017/07271* (2013.01); *A61B 2017/07285* (2013.01)

(58) Field of Classification Search
 CPC ............ A61B 17/072; A61B 17/07207; A61B 2017/07271; A61B 2017/07285; A61B 2017/07278
 See application file for complete search history.

(56) References Cited

U.S. PATENT DOCUMENTS 5,535,935 A * 7/1996 Vidal .................... A61B 17/064
 227/175.2
5,826,776 A * 10/1998 Schulze ........... A61B 17/07207
 227/176.1
(Continued)

FOREIGN PATENT DOCUMENTS

CN 101856255 A 10/2010
CN 203564286 U 4/2014
(Continued)

OTHER PUBLICATIONS

ISR for PCT/CN2015/088102, dated Dec. 1, 2015.

*Primary Examiner* — Andrew M Tecco
(74) *Attorney, Agent, or Firm* — Michael Fainberg; Arent Fox LLP

(57) ABSTRACT

An end effector and staple cartridge assembly thereof, and surgical instrument; the staple cartridge assembly includes a cartridge, a wedge and a cutting knife; the wedge is slidably mounted to the cartridge; the cutting knife is positioned in a cutting slot of the cartridge; one end of the cutting knife that is distal from a staple exiting surface of the cartridge is pivotally connected to the wedge via a pin; an axial of the pin is perpendicular to the cutting slot; the proximal surface of the cutting knife contacts against a pushing surface; an elastic resetting member is arranged between the cutting knife and the wedge.

16 Claims, 3 Drawing Sheets

(56) References Cited

U.S. PATENT DOCUMENTS

| | | | | |
|---|---|---|---|---|
| 7,918,230 B2* | 4/2011 | Whitman | ......... | A61B 17/07207 |
| | | | | 128/898 |
| 8,672,209 B2* | 3/2014 | Crainich | .......... | A61B 17/07207 |
| | | | | 227/178.1 |
| 2004/0199181 A1* | 10/2004 | Knodel | ............ | A61B 17/07207 |
| | | | | 606/139 |
| 2010/0294829 A1 | 11/2010 | Giordano et al. | | |

FOREIGN PATENT DOCUMENTS

| | | |
|---|---|---|
| CN | 103860222 A | 6/2014 |
| CN | 204106084 U | 1/2015 |

\* cited by examiner

END EFFECTOR, CARTRIDGE ASSEMBLY THEREOF, AND SURGICAL INSTRUMENT

This application claims priority to and is a continuation of International Application No. PCT/CN2015/088102, filed on Aug. 26, 2015, designating the United States, and claiming the priorities of Chinese Patent Application No. 201410461885.5 filed with the State Intellectual Property Office of People's Republic of China on Sep. 12, 2014, and Chinese Patent Application No. 201420522487.5 filed with the State Intellectual Property Office of People's Republic of China on Sep. 12, 2014, both of which are hereby incorporated by reference in their entireties.

FIELD

The present disclosure relates to medical instruments, particularly to an end effector, a cartridge assembly thereof and a surgical instrument.

BACKGROUND

Endoscopic and laparoscopic surgical instruments are often preferred over traditional open surgical devices since a smaller incision tends to reduce the post-operative recovery time and complications.

A surgical instrument includes a handle portion and an end effector, the handle portion includes a stationary handle configured to be held by an operator, the distal end (the end that is closer to the operator is the proximal end and the end that is farther from the operator is the distal end) of the handle portion is connected with the end effector through an elongated portion, and the end effector includes an anvil assembly and a cartridge assembly including a cartridge for holding surgical staples.

The surgical instrument includes a cutting knife configured to cut human tissues of a surgical site, and the sharpness of the cutting knife is a key parameter for cutting and suturing.

However, generally, the cartridge assembly of the end effector is single use unit, while the cutting knife needs to be reused. The repeated use of the cutting knife would seriously affect the sharpness of the blade, thus reducing the quality of the surgery and increasing the risk of medical care.

SUMMARY

The present disclosure provides an end effector and a cartridge assembly thereof, and a surgical instrument, while through one replacement (also called reload) of the cartridge assembly, both the cartridge and the cutting knife can be replaced, thus improving the safety of the surgical instrument and reducing medical risk.

In order to attain the object above, the present disclosure provides the following technical solutions:

A cartridge assembly, comprising a cartridge, a wedge and a cutting knife; wherein, the wedge is slidably mounted to the cartridge and configured to be slidable from a proximal end to a distal end of the cartridge; the cutting knife is positioned in a cutting slot provided in the cartridge; one end of the cutting knife that is opposite to a staple exiting surface of the cartridge is pivotally connected to the wedge via a pin; an axis of the pin is perpendicular to the cutting slot; a proximal surface of the cutting knife contacts against a knife pushing bar of a surgical instrument; and an elastic resetting member is arranged between the cutting knife and the wedge, under which a cutting edge portion of the cutting knife is received within the cutting slot of the cartridge before being urged by the knife pushing bar, and the cutting knife rotates about the pin into a cutting position when being urged by the knife pushing bar.

Preferably, the distal end of the cartridge engages with the wedge through a flexible limiting mechanism.

Preferably, the flexible limiting mechanism comprises at least one flexible projection provided on the cutting slot of the cartridge; and at least one limiting slot provided in the wedge, wherein the flexible projection extends into the limiting slot to maintain the engagement between the wedge and the cartridge.

Preferably, the elastic resetting member is a spring, one end of which is mounted to the wedge and other end is mounted to the cutting knife.

Preferably, the elastic resetting member is an elastic sheet, one side of which is connected to the wedge and other side is connected to the cutting knife.

Preferably, the present disclosure also provides an end effector, which comprising an anvil assembly, wherein the end effector further comprises a cartridge assembly according to any one of above-mentioned cartridge assembly, and the anvil assembly is mounted with respect to the cartridge assembly.

Preferably, the present disclosure also provides a surgical instrument, which comprising a handle portion and an elongated portion, wherein a proximal end of the elongated portion is mounted on the handle portion and a knife pushing bar is provided in the elongated portion, wherein further comprises an end effector according to the above-mentioned end effector, wherein the proximal ends of the cartridge assembly and the anvil assembly are mounted on a distal end of the elongated portion.

Preferably, the surgical instrument mentioned above is an endoscopic stapler.

REFERENCE NUMERALS

1—cartridge assembly
2—anvil assembly

3—knife pushing bar
11—cutting knife
12—wedge
13—pin
14—cartridge
15—elastic resetting member
141—cutting slot
142—flexible projection

DETAILED DESCRIPTION

The technical solutions according to the embodiments of the present disclosure will be described below clearly and fully with reference to the drawings in the embodiments of the present disclosure, and apparently the embodiments described below are only a part but not all of the embodiments of the present disclosure. Based upon the embodiments here of the present disclosure, all the other embodiments which can occur to those skilled in the art without any inventive effort shall fall into the scope of the present disclosure.

The present disclosure provides an end effector and a cartridge assembly thereof and a surgical instrument. Herein, relevant concepts of the end effector and the surgical instrument are introduced so as to facilitate the description of the cartridge assembly of any one of the embodiments of the present disclosure, which will not be described again in the present disclosure.

Moreover, as used herein, the term "distal" will refer to the portion of the instrument that is farther from the operator and the term "proximal" will refer to the portion of the instrument that is closer to the operator.

Figure 1:
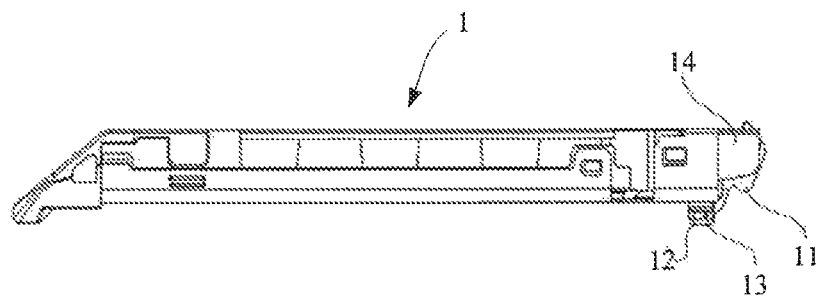
FIG. 1 is a schematic view of one embodiment of a cartridge assembly according to the present disclosure.

Referring to FIG. 1, which shows the structure of one embodiment of a cartridge assembly according to the present disclosure.

Figure 2:
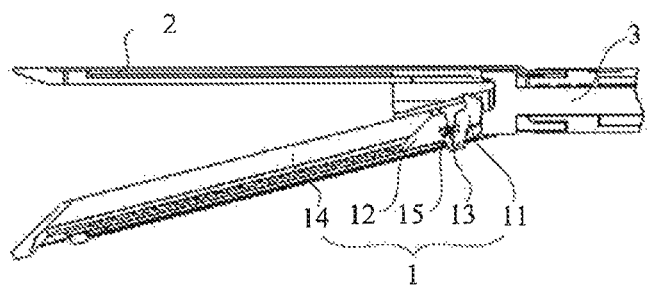
FIG. 2 shows the cutting knife being received within the cartridge while the end effector of the surgical instrument has not been fired according to embodiments of the present disclosure.

According to one of the embodiments of the present disclosure, the surgical instrument comprises a handle portion and an elongated portion, where the proximal end of the elongated portion is mounted to the handle portion and a knife pushing bar is provided therein. The surgical instrument further includes an end effector having a cartridge assembly and an anvil assembly, the proximal ends of which are mounted on the distal end of the elongated portion, respectively. As illustrated in FIG. 1 and FIG. 2, the end effector includes the cartridge assembly 1 and the anvil assembly 2. The cartridge assembly 1 includes a cartridge 14 and a cutting knife 11, both of which are disposable (i.e. for single use), so as to be replaceable as replacing the cartridge assembly 1 of the end effector. Thus, a worn cutting knife 11 can be replaced along with replacement of a cartridge assembly.

Preferably, the surgical instrument of one of the embodiments of the present disclosure is an endoscopic stapler.

Figure 3:
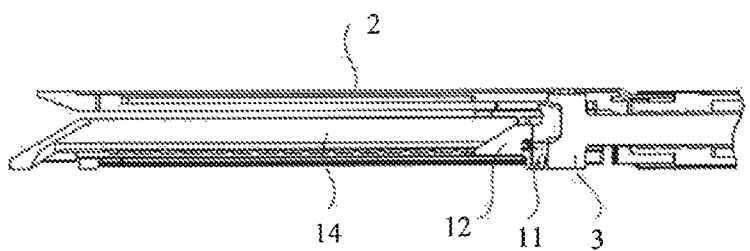
FIG. 3 shows the cutting knife of the cartridge assembly being rotated by the knife pushing bar to its cutting position, while the end effector of the surgical instrument has not being fired according to embodiments of the present disclosure.
Figure 4:
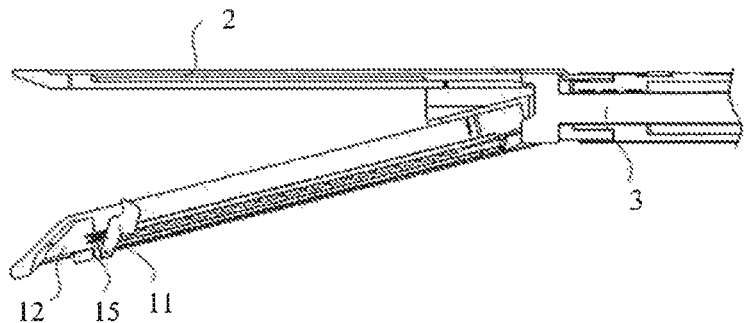
FIG. 4 shows the cutting knife being received within the cartridge after the end effector of the surgical instrument has been performed cutting according to embodiments of the present disclosure.
Figure 5:
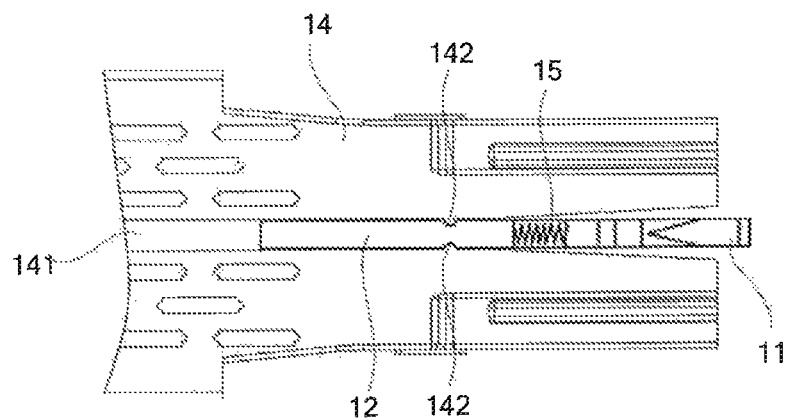
FIG. 5 shows the cooperation between a wedge and the cartridge when the end effector of the surgical instrument has not been performed cutting according to embodiments of the present disclosure.

Referring to FIG. 1 and FIG. 2-5, FIG. 2 shows the cutting knife being received within the cartridge while the end effector of the surgical instrument has not been fired according to embodiments of the present disclosure; FIG. 3 shows the cutting knife of the cartridge assembly being rotated by the knife pushing bar to its cutting position, while the end effector of the surgical instrument has not being fired according to embodiments of the present disclosure; FIG. 4 shows the cutting knife being received within the cartridge after the end effector of the surgical instrument has been performed cutting according to embodiments of the present disclosure; and FIG. 5 shows the cooperation between a wedge and the cartridge when the end effector of the surgical instrument has not been performed cutting according to embodiments of the present disclosure.

As illustrated in FIG. 1, the cartridge assembly 1 of the end effector according to one of embodiments of the present disclosure, includes the cartridge 14, the wedge 12 and the cutting knife 11, where the wedge 12 is slidably mounted to the cartridge 14 as well as slidable from the proximal end of the cartridge 14 to the distal end thereof.

As illustrated in FIG. 2 to FIG. 5, the cutting knife 11 is positioned in a cutting slot 141 provided in the cartridge 14; one end of the cutting knife 11 which is opposite to a staple exiting surface of the cartridge 14 is pivotally connected to the wedge 12 via a pin 13; an axis of the pin 13 is perpendicular to the cutting slot 141; an elastic resetting member 15 is provided between the cutting knife 11 and the wedge 12; and the cutting edge portion of the cutting knife 11 is biased or received within the cutting slot 141 of the cartridge 14 under the elastic resetting member 15 when the cutting knife 11 is not pushed by the knife pushing bar 3, and the cutting knife 11 can be rotated about the pin 13 into a cutting position when being urged by the knife pushing bar 3.

As illustrated in FIG. 5, the cutting knife 11 of the cartridge assembly of one embodiment of the present disclosure is positioned in the cutting slot 141 of the cartridge 14; one end of the cutting knife 11 that is opposite to the staple exiting surface of the cartridge 14 is pivotally connected to the wedge 12 via the pin 13; the elastic resetting member 15 is arranged between the cutting knife 11 and the wedge 12. As illustrated in FIG. 2, when the cutting knife 11 is not urged by the knife pushing bar 3 of the surgical instrument, the cutting edge portion thereof is received within the cartridge 14 under a force of the elastic resetting member 15, so as to prevent the cutting knife 11 from hurting the operator during loading of the cartridge assembly 1. Referring to FIG. 3, how the surgical instrument is performed cutting and suturing will be described as follows: firstly, closing the anvil assembly 2 and the cartridge assembly 1 of the end effector through a corresponding drive assembly so as to clamp the tissue grasped between the anvil assembly and the cartridge assembly; then distally advancing the knife pushing bar 3 till the distal face thereof contacts against the cutting knife 11, and as being pushed by the knife pushing bar 3, the cutting knife 11 overcomes the resetting force of the elastic resetting member 15 and rotates about the pin 13 arranged between the cutting knife 11 and the cartridge 14 so as to reach the cutting position, where the cutting edge portion of the cutting knife 11 is exposed out of the cartridge 14; further, distally advancing the knife pushing bar 3, and the pushing force of the knife pushing bar 3 is transmitted to the wedge 12 through the cutting knife 11, allowing the wedge 12 to move distally along with the culling knife 11 for cutting and suturing of the tissue. As illustrated in FIG. 4, after the cutting and suturing have been completed, the knife pushing bar 3 moves proximally and resets through the corresponding assembly; meanwhile, the cutting knife 11 rotates about the pin 13 arranged between the cutting knife 11 and the wedge 12 under the resetting force of the elastic resetting member 15 till the cutting edge portion of the cutting knife 11 is received within the cartridge 14, so as to prevent the cutting edge portion of the cutting knife 11 from hurting tissues as well as from hurting the operator during replacement of the cartridge assembly 1.

Therefore, it is operable to replace the cutting knife 11 of the cartridge assembly 1 of one embodiment of the present disclosure along with replacement of the cartridge 14. The cutting knife 11 of the cartridge assembly 1 is for single use, thus, the worn cutting knife 11 can be replaced along with replacement of the cartridge assembly 1 during usage of the surgical instrument.

Also, an end effector having the cartridge assembly 1 is provided in one of embodiments of the present disclosure, so that through one replacement (also called reload) of the cartridge assembly 1, both the cartridge 14 and the cutting knife 11 can be replaced, while all the other parts apart except for the cartridge assembly 1 of the end effector could be reused. Therefore, it is not only that the worn cutting knife 11 can be replaced along with replacement of the cartridge assembly 1, but also remains as many as possible parts of the end effector reusable, so that costs of the product can be reduced.

In a preferred embodiment, the proximal end of the cartridge 14 engages with the wedge 12 through a flexible limiting mechanism.

The flexible limiting mechanism is configured to allow the cutting knife 11 to rotate into the cutting position when it contacts the knife pushing bar 3 without pushing the wedge 12. After the cutting knife 11 has rotated to the cutting position, the knife pushing bar 3 continues to move distally, and the cutting knife 11 transmits the force of the knife pushing bar 3 to the wedge 12 till the wedge 12 is free from limitation of the flexible limiting mechanism so as to further push the wedge 12 to move distally.

Preferably, as illustrated in FIG. 5, the flexible limiting mechanism includes:

at least one flexible projection 142 arranged on the cutting slot 141 of the cartridge 14;

at least one limiting slot provided on the wedge 12, wherein the flexible projection 142 extends into the limiting slot so as to limit the position of the wedge 12 with respect to the cartridge 14.

Of course, there are various embodiments of the flexible limiting mechanism arranged between the cartridge 14 and the wedge 12, which would not be described here anymore.

Figure 6:
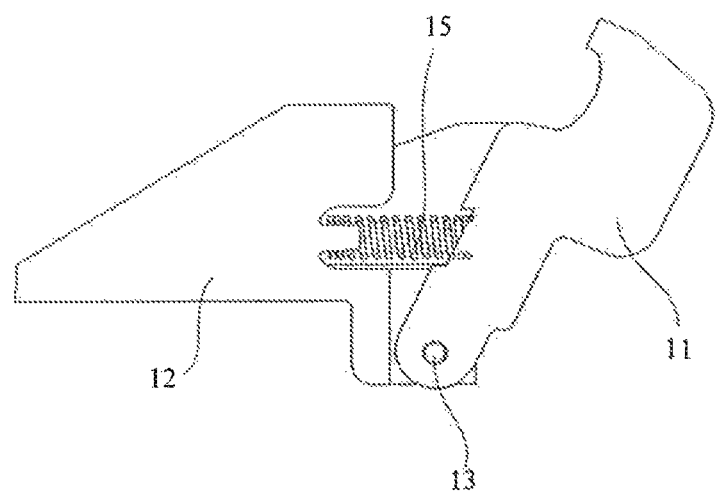
FIG. 6 is a schematic structural diagram of the cartridge assembly's elastic resetting member when the member is a spring, according to embodiments of the present disclosure.

On the basis of the various embodiments above, there are various types of the elastic resetting member 15 arranged between the cutting knife 11 and the wedge 12:

As illustrated in FIG. 6, the elastic resetting member 15 of one of embodiments of the present disclosure is configured as a spring, one end of which is mounted to the wedge 12 and the other end is mounted to the cutting knife 11.

Figure 7:
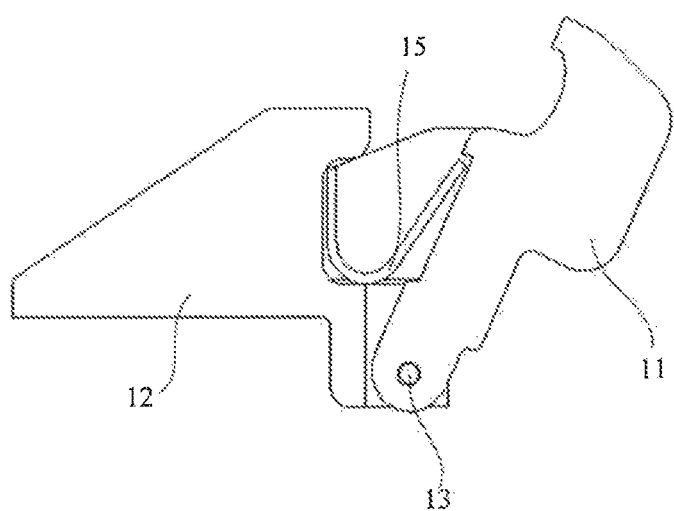
FIG. 7 is a schematic structural diagram of the cartridge assembly's elastic resetting member when the member is an elastic sheet, according to embodiments of the present disclosure.

As illustrated in FIG. 7, the elastic resetting member 15 of one of embodiments of the present disclosure is configured as an elastic sheet, one side of which is connected to the wedge 12 and the other side is connected to the cutting knife 11.

Evidently those skilled in the art can make various modifications and variations to the present disclosure without departing from the spirit and scope of the present disclosure. Thus the present disclosure is also intended to encompass these modifications and variations thereto so long as the modifications and variations come into the scope of the claims appended to the present disclosure and their equivalents.

I claim:

1. A cartridge assembly, comprising a cartridge, a wedge and a cutting knife; wherein,
    the wedge is slidably mounted to the cartridge and configured to be slidable from a proximal end to a distal end of the cartridge;
    the cutting knife is positioned in a cutting slot provided in the cartridge; one end of the cutting knife that is opposite to a staple exiting surface of the cartridge is pivotally connected to the wedge via a pin; an axis of the pin is perpendicular to the cutting slot; a proximal surface of the cutting knife contacts against a knife pushing bar of a surgical instrument; and
    an elastic resetting member is arranged between the cutting knife and the wedge, under which a cutting edge portion of the cutting knife is received within the cutting slot of the cartridge before being urged by the knife pushing bar, and the cutting knife rotates about the pin into a cutting position when being urged by the knife pushing bar.

2. The cartridge assembly according to claim 1, wherein, the distal end of the cartridge engages with the wedge through a flexible limiting mechanism.

3. The cartridge assembly according to claim 2, wherein, the flexible limiting mechanism comprises at least one flexible projection provided on the cutting slot of the cartridge; and at least one limiting slot provided in the wedge, wherein the flexible projection extends into the limiting slot to maintain the engagement between the wedge and the cartridge.

4. The cartridge assembly according to claim 1, wherein the elastic resetting member is a spring, one end of which is mounted to the wedge and other end is mounted to the cutting knife.

5. The cartridge assembly according to claim 1, wherein the elastic resetting member is an elastic sheet, one side of which is connected to the wedge and other side is connected to the cutting knife.

6. An end effector, comprising an anvil assembly, wherein the end effector further comprises a cartridge assembly according to claim 1, and the anvil assembly is mounted with respect to the cartridge assembly.

7. The end effector according to claim 6, wherein, the distal end of the cartridge engages with the wedge through a flexible limiting mechanism.

8. The end effector according to claim 7, wherein, the flexible limiting mechanism comprises at least one flexible projection provided on the cutting slot of the cartridge; and at least one limiting slot provided in the wedge, wherein the flexible projection extends into the limiting slot to maintain the engagement between the wedge and the cartridge.

9. The end effector according to claim 6, wherein the elastic resetting member is a spring, one end of which is mounted to the wedge and other end is mounted to the cutting knife.

10. The end effector according to claim 6, wherein the elastic resetting member is an elastic sheet, one side of which is connected to the wedge and other side is connected to the cutting knife.

11. A surgical instrument, comprising a handle portion and an elongated portion, wherein a proximal end of the elongated portion is mounted on the handle portion and a knife pushing bar is provided in the elongated portion, wherein further comprises an end effector according to claim 6, wherein the proximal ends of the cartridge assembly and the anvil assembly are mounted on a distal end of the elongated portion.

12. The surgical instrument according to claim 11, wherein the surgical instrument is an endoscopic stapler.

13. The surgical instrument according to claim 11, wherein, the distal end of the cartridge engages with the wedge through a flexible limiting mechanism.

14. The surgical instrument according to claim 13, wherein, the flexible limiting mechanism comprises at least one flexible projection provided on the cutting slot of the cartridge; and at least one limiting slot provided in the wedge, wherein the flexible projection extends into the limiting slot to maintain the engagement between the wedge and the cartridge.

15. The surgical instrument according to claim 11, wherein the elastic resetting member is a spring, one end of which is mounted to the wedge and other end is mounted to the cutting knife.

16. The surgical instrument according to claim 11, wherein the elastic resetting member is an elastic sheet, one side of which is connected to the wedge and other side is connected to the cutting knife.

* * * * *